US010161861B2

(12) United States Patent
Zhang et al.

(10) Patent No.: US 10,161,861 B2
(45) Date of Patent: Dec. 25, 2018

(54) COMPACT DEVICE FOR SENSING A LIQUID WITH ENERGY HARVESTING FROM LIQUID MOTION

(71) Applicant: Hong Kong Applied Science and Technology Research Institute Company Limited, Hong Kong (HK)

(72) Inventors: Chun Zhang, Hong Kong (HK); Ngok Man Sze, Hong Kong (HK); Luis Ng, Hong Kong (HK)

(73) Assignee: Hong Kong Applied Science and Technology Research Institute Company Limited, Hong Kong (CN)

( * ) Notice: Subject to any disclaimer, the term of this patent is extended or adjusted under 35 U.S.C. 154(b) by 0 days.

(21) Appl. No.: 15/377,643

(22) Filed: Dec. 13, 2016

(65) Prior Publication Data
US 2018/0164210 A1 Jun. 14, 2018

(51) Int. Cl.
*G01N 21/00* (2006.01)
*G01N 21/3577* (2014.01)
(Continued)

(52) U.S. Cl.
CPC ........ *G01N 21/3577* (2013.01); *G01J 3/0264* (2013.01); *G01J 3/0283* (2013.01);
(Continued)

(58) Field of Classification Search
CPC ........ G01J 3/0283; G01J 3/44; G01N 21/532; G01N 21/39; G01N 2201/0612; G01N 21/3151
(Continued)

(56) References Cited

U.S. PATENT DOCUMENTS 4,311,398 A * 1/1982 Gerjets ................. B41J 19/202
400/144.2
6,307,198 B1 * 10/2001 Asakura ............ B32B 17/10036
250/227.25
(Continued)

FOREIGN PATENT DOCUMENTS

| CN | 1948951 A | 4/2007 |
|---|---|---|
| CN | 103776787 A | 5/2014 |
| CN | 205157414 U | 4/2016 |
| CN | 105784042 A | 7/2016 |
| WO | 2001046676 A2 | 6/2001 |

OTHER PUBLICATIONS

International Search Report and Written Opinion of PCT application No. PCT/CN2016/112072 issued from the International Search Authority dated Sep. 14, 2017.

*Primary Examiner* — Isiaka Akanbi
(74) *Attorney, Agent, or Firm* — Norton Rose Fulbright US LLP

(57) ABSTRACT

A compact device useful for measuring an absorption spectrum of a liquid, such as water with organic contaminants, is provided. The device comprises an array of light emitting diodes (LEDs) each emitting light with a unique spectral peak. A reflector shaped as a half ellipsoid reflects the emitted light to form a reference beam. The reflector has an opening to allow part of the emitted light to form a measurement beam after passing through the liquid. Two photodetectors measure the reference beam and the measurement beam to give a reference intensity and a measured intensity, respectively. The LEDs sequentially emit showers of light one-by-one, giving plural pairs of reference and measured intensities for estimating the absorption spectrum. The device receives energy from a separate power-providing device through wireless power transfer. The power-providing device harvests motional energy of the flowing liquid to generate electrical energy.

20 Claims, 6 Drawing Sheets

(51) Int. Cl.
*G01N 33/18* (2006.01)
*G01N 21/33* (2006.01)
*G01J 3/42* (2006.01)
*G01J 3/02* (2006.01)
*G01N 21/25* (2006.01)

(52) U.S. Cl.
CPC ............ *G01J 3/42* (2013.01); *G01N 21/255* (2013.01); *G01N 21/33* (2013.01); *G01N 33/1826* (2013.01); *G01N 2201/0621* (2013.01); *G01N 2201/0627* (2013.01); *G01N 2201/0636* (2013.01); *G01N 2201/0637* (2013.01); *G01N 2201/1211* (2013.01)

(58) Field of Classification Search
USPC .................................................. 356/436–438
See application file for complete search history.

(56) References Cited

U.S. PATENT DOCUMENTS

| | | |
|---|---|---|
| 6,956,648 B2 | 10/2005 | Loicht et al. |
| 7,336,356 B2 | 2/2008 | Vannuffelen et al. |
| 7,428,995 B1 | 9/2008 | Stern et al. |
| 9,291,504 B2 | 3/2016 | Goldring et al. |
| 2010/0053621 A1* | 3/2010 | Olson ............... A61L 2/208 356/437 |
| 2010/0208261 A1 | 8/2010 | Sens et al. |
| 2012/0228519 A1* | 9/2012 | Gilmore ............ G01N 21/645 250/459.1 |
| 2013/0020480 A1 | 1/2013 | Ford et al. |
| 2015/0268159 A1* | 9/2015 | Tabaru ............... G01N 21/39 356/437 |
| 2017/0191020 A1* | 7/2017 | Recht ............... C12Q 1/04 |

* cited by examiner

COMPACT DEVICE FOR SENSING A LIQUID WITH ENERGY HARVESTING FROM LIQUID MOTION

FIELD OF THE INVENTION

The present invention generally relates to optical sensing of a liquid. In particular, the present invention relates to a device for measuring absorption of light by a liquid and a system using the device to measure an absorption spectrum of the liquid with harvesting motion energy of the flowing liquid for fully or partially powering the device.

BACKGROUND

The quality of drinking water can be assessed by measuring an absorption spectrum of a water sample that may be contaminated by organic contaminants such as toluene. It is known in the art that ultraviolet-visible (UV-vis) and near infrared (NIR) spectroscopic methods are useful to detect such organic contaminants.

With a growing demand on assessing water quality, it is often desirable to have compact measurement devices to simultaneously, continuously and conveniently obtain and analyze water samples from many different locations. Besides, each measurement device is preferred to fit in a limited space such as a water pipe, to be light-weight and power-efficient, and to have a wide spectral and dynamic range.

In U.S. Pat. No. 6,956,648 and WO2001/46676, a miniaturized device for probing a liquid is disclosed. Two light beams are generated from a light source. One light beam passes through the liquid to give a measurement beam, and another one serves as a reference beam. A beam selector is used to select one of the two beams for sending to a spectrometer. As the spectrometer is still large, it is not convenient in operation, even if the spectrometer is remotely linked to the device through a light guide. Although reduced-size spectrometers have been developed in, e.g., U.S. Pat. No. 9,291,504, such spectrometers may still be considered too large if an integrated unit combining one such spectrometer and a light source is operated by immersing the unit into the liquid flowing along a pipe.

There is a need for a compact device for sensing a liquid in general and water in particular so that an absorption spectrum of the liquid is obtained.

SUMMARY OF THE INVENTION

The present invention provides a device for sensing a pre-determined liquid, offering an advantage that it is possible to make the device compact as well as reduce the material cost in comparison to an alternative design that uses a spectrometer.

The sensing device comprises a sensing unit. The sensing unit comprises a light emitting diode (LED) array for emitting light. The LED array comprises plural LEDs. In general, the LEDs have the following characteristics. Each of the LEDs is configured to generate a shower of light having an emission spectrum having a single dominant spectral peak at a peak wavelength. The peak wavelengths of the LEDs are distinct. The sensing device further comprises a reflector for reflecting light emitted from the LED array. The reflector includes an opening for allowing a part of the emitted light to exit the reflector and form a probe light beam for sensing the liquid. In addition, the reflector is shaped to be substantially similar to one half of an ellipsoid except on the opening. The ellipsoid has a first focus and a second focus. The LED array is located at the first focus so that the emitted light incident on the reflector is reflected to the second focus, causing the emitted light after reflection to be refocused at the second focus. A first photodetector (PD) located at the second focus is used for measuring an intensity of the refocused emitted light to thereby yield a reference intensity. A second PD is used for measuring an intensity of the probe light beam received after the probe light beam passes through the liquid to thereby yield a measured intensity. The LED array and the first PD are mounted to a substrate. The reflector is located on the substrate such that an enclosed space between the reflector and the substrate is formed. The sensing unit further comprises a sealer formed by filling the enclosed space with a substantially-transparent sealing material impermeable to the liquid for sealing the LED array and the first PD from the liquid. The sealer is further prepared to have a convex surface on the opening. The convex surface is shaped to refract the emitted light incident on the opening to form the probe light beam. In addition, the convex surface is shaped such that the probe light beam is substantially collimated when the device is immersed in the liquid.

The sensing device further comprises a control circuit for controlling at least the LEDs, the first PD and the second PD. The control circuit is configured to control the LEDs to sequentially generate the showers of light one-by-one such that plural pairs of intensity values are generated and received by the control circuit. Each pair of intensity values consists of the measured intensity and the reference intensity both obtained when an individual LED alone generates the emitted light.

In addition, the sensing device further comprises a temperature sensor for measuring a temperature of the LED array. The temperature sensor is controllable by the control circuit.

The sensing device may further include a processor for estimating the absorption spectrum of the liquid according to the pairs of intensity values. Alternatively, an external computing device may be used to receive the pairs of intensity values from the sensing device, and then estimate the absorption spectrum.

The sensing device may also be configured to utilize motional energy of the liquid for fully or partially powering the sensing device. In this regard, a power-providing device is used to provide energy to the sensing device through wireless power transfer (WPT) when both the sensing device and the power-providing device are immersed in the liquid. The sensing device comprises one or more on-board rechargeable batteries, and a WPT receiver for capturing wirelessly-transmitted electrical energy and using the captured electrical energy to recharge the one or more rechargeable batteries. The power-providing device comprises a hydroelectric power generator for harvesting motional energy of the liquid and converting the motional energy into electrical energy, and a WPT transmitter for wirelessly delivering the electrical energy to the WPT receiver.

By using the disclosed sensing device, the absorption spectrum of the liquid may be estimated by a method as follows. In the method, the LEDs sequentially generate the showers of light one-by-one so as to generate the plural pairs of intensity values. The temperature of the LED array is also measured. For an individual LED, compute a first scaling factor of an asymmetric Gaussian spectrum model for characterizing a first spectral distribution of the reference intensity according to the reference intensity and a set of pre-determined model parameters of the spectrum model. The set of pre-determined model parameters is specific to the individual LED, and is selected from a larger set of pre-determined model parameters based on the measured temperature. For the individual LED, also compute a second scaling factor of the spectrum model for characterizing a second spectral distribution of the measured intensity according to the measured intensity and the set of pre-determined model parameters. The computation of the first and second scaling factors is repeated for all the LEDs in the LED array. As a result, a plurality of first spectral distributions and a plurality of second spectral distributions are obtained. The absorption spectrum is then determined according to the plurality of first spectral distributions and the plurality of second spectral distributions.

Other aspects of the present invention are disclosed as illustrated by the embodiments hereinafter.

BRIEF DESCRIPTION OF THE DRAWINGS

FIG. 3A depicts calibrating emission spectra of an individual LED under different temperatures in order to fit each emission spectrum to an asymmetric Gaussian spectrum model, FIG. 3B depicts performing a reference measurement in air for obtaining reference spectra that are obtained at the first and second PDs, and FIG. 3C depicts performing an on-site measurement for obtaining the absorption spectrum of the liquid.

DETAILED DESCRIPTION

In one practical implementation of a spectrometer used in UV-vis or NIR spectroscopy, the spectrometer includes a grating and an imaging sensor. The grating is used to diffract an incoming light beam, and the resultant diffraction pattern is imaged by the imaging sensor such as a sensitive charge-coupled device (CCD). In order to achieve necessary spectral resolution, the diffraction configuration, i.e. the grating size and the distance between the grating and the CCD, is somewhat large so that it is not easy to miniaturize the spectrometer. If it is not required to generate the diffraction pattern without losing spectral information in detecting the incoming light beam, an equipment size can be reduced. Furthermore, measuring an absorption spectrum of a water sample involves two light beams, i.e. the measurement beam and the reference beam as mentioned above. A beam selector, often implemented as a mechanical chopper, is used for delivering a selected one of these two beams to the spectrometer. Removal of the mechanical chopper is desirable in further reducing the equipment size. Based on the aforementioned two observations, the Inventors have considered using a few number of photodetectors, such as photodiodes, to perform a spectroscopic measurement. Using the photodetectors instead of the spectrometer not only makes a water-sensing device compact, but also reduces the material cost. The present invention is developed by utilizing such advantages offered by the photodetectors.

The present invention provides a device for sensing a pre-determined liquid, offering an advantage that it is possible to make the device compact as well as reduce the material cost in comparison to an alternative design that uses a spectrometer. The sensing of the liquid performed by the device directly or indirectly leads to an absorption spectrum of the liquid. That is, the device may directly output the absorption spectrum, or the device may produce measurement data that after further computation or data processing on the measurement data by another computing device, lead to the absorption spectrum.

Although the present invention has a major practical application of detecting organic contaminants in water, the present invention is not limited only to the case that the pre-determined liquid is substantially composed of water. The present invention is applicable to any liquid that does not hamper the operation of the sensing device, e.g., fruit juice.

The sensing device as disclosed herein comprises a sensing unit for optically probing the liquid. The sensing unit is illustrated with the aid of FIG. 1, which depicts a cross-sectional view of an exemplary sensing unit 100.

Figure 1:
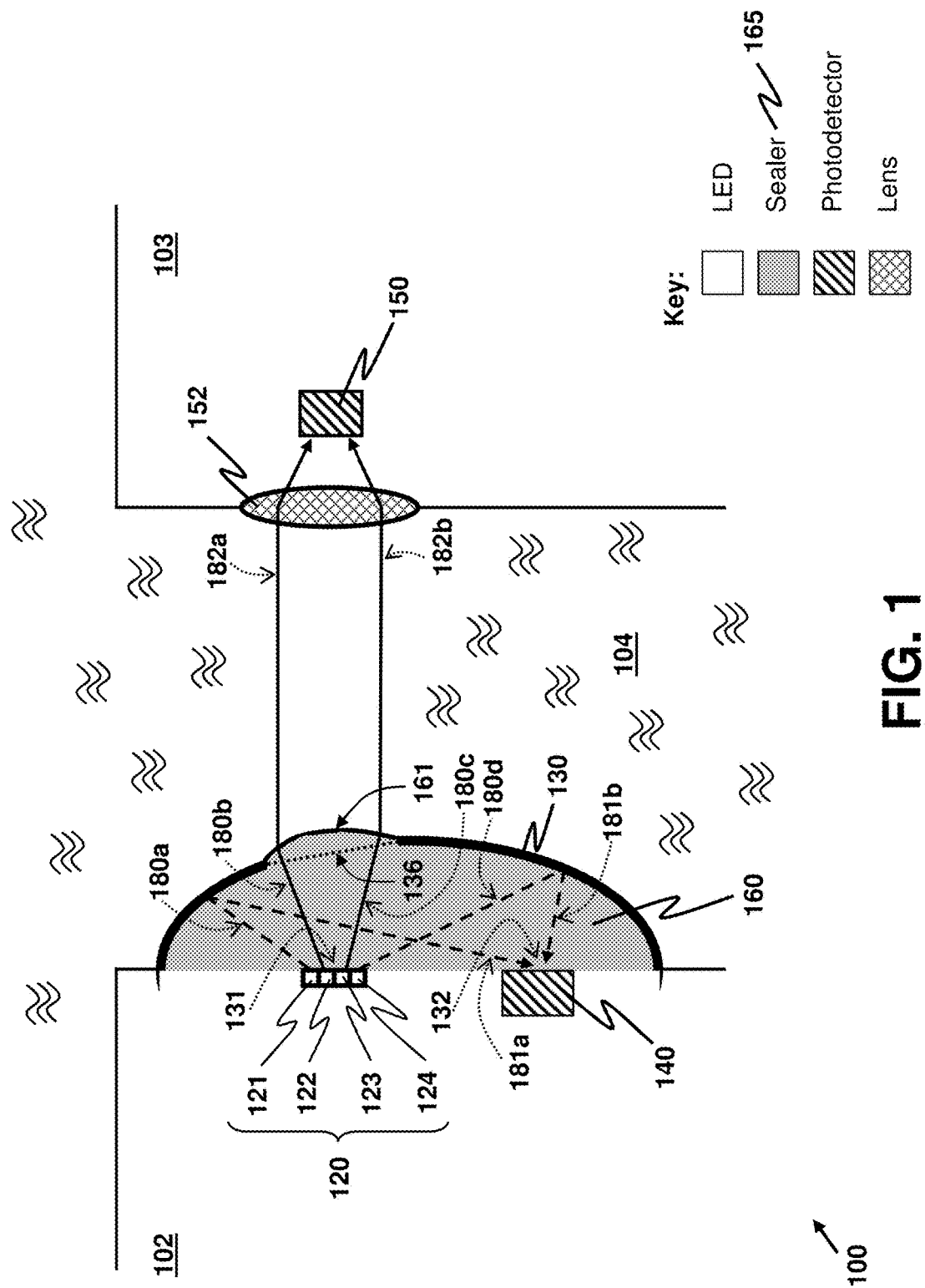
FIG. 1 depicts a cross-sectional view of a sensing unit in accordance with an exemplary embodiment of the invention.

The sensing unit 100 comprises a light emitting diode (LED) array 120 as a light source for emitting light for probing the liquid. The LED array 120 comprises plural LEDs 121-124. Although only four LEDs 121-124 are depicted in FIG. 1 for illustration, the present invention is not limited to using only four LEDs; any number of LEDs greater than one may be used in the LED array. The inclusion of more than one LED in the LED array 120 is because only one LED rarely provides a light beam having an emission spectrum sufficiently wide enough to cover a spectrum of interest in probing the liquid. For example, in detecting organic contaminants in water, the spectrum of interest sometimes covers the UV region, the visible region and the NIR region, and may have a wide spectral range of 200 nm to 2500 nm. More-than-one LEDs in the LED array 120 are advantageously used for covering the entire spectrum of interest. In general, each of the LEDs 121-124 is configured to generate a shower of light having an emission spectrum, where the emission spectrum has a single dominant spectral peak at a peak wavelength. In particular, the peak wavelengths of the LEDs 121-124 are distinct. These peak wavelengths are purposely made distinct such that the emission spectra of the LEDs 121-124 collectively cover the entire spectrum of interest. It is obvious to those skilled in the art that more-than-one component LEDs having the same peak wavelength may be grouped together to form one LED that emits light at this peak wavelength with a greater power when the component LEDs are driven simultaneously. Herein a LED having a peak wavelength may include plural component LEDs having this peak wavelength, or may only have one single component LED. It is possible that different LEDs in the LED array 120 have partially overlapped emission spectra, causing ambiguity in identifying absorption peaks of the liquid. The Inventors have developed a solution to this ambiguity issue and the solution will be expounded later.

To make the sensing unit 100 compact (enabling the sensing device to be compact too), the sensing unit 100 utilizes a reflector 130 to give a measurement beam and a reference beam from light emitted from the LED array 120 (corresponding to light rays 180a-d). The reflector 130 is used for reflecting the emitted light 180a-d. Advantageously and purposely, the reflector 130 includes an opening 136 for allowing a part of the emitted light (i.e. the light rays 180b, 180c) to exit the reflector 130 and form a probe light beam (corresponding to light rays 182a, 182b) for sensing the liquid. The liquid is allowed to fill in a liquid-retaining space 104, realized as, e.g., an open chamber or a channel, such that the probe light beam 182a-b passes through the liquid in the liquid-retaining space 104. Note that the measurement beam is formed after the probe light beam 182a-b passes through the liquid. Furthermore, the reflector 130 is shaped to be substantially similar to one half of an ellipsoid except on the opening 136, where the ellipsoid has a first focus 131 and a second focus 132. The LED array 120 is located at the first focus 131. As a known property of the ellipsoid, the emitted light incident on the reflector 130 (i.e. the light rays 180a, 180d) is reflected to the second focus 132. It causes the emitted light after reflection (i.e. light rays 181a, 181b) to be refocused at the second focus 132, thereby forming a refocused emitted light 181a-b.

The sensing unit 100 uses a first photodetector (PD) 140 located at the second focus 132 for measuring an intensity of the refocused emitted light 181a-b. As will be shown, the refocused emitted light 181a-b does not travel through the liquid. Hence, the refocused emitted light 181a-b serves as the reference beam. The intensity of the refocused emitted light 181a-b as measured by the first PD 140 is referred to as a reference intensity.

Furthermore, the sensing unit 100 uses a second PD 150 for measuring an intensity of the measurement beam (viz., the probe light beam 182a-b received by the second PD 150 after the probe light beam 182a-b passes through the liquid) to thereby yield a measured intensity. A focusing lens 152, or alternatively an equivalent polymer sealer similar to the sealer 165 to be described later, is usually installed on or over a sensing area of the second PD 150 in order to focus the measurement beam onto the sensing area.

Each of the two PDs 140 and 150 may comprise one or more individual photodiodes responsive to the spectral range of interest. For instance, a Si photodiode is responsive to 200-1100 nm and an InGaAs photodiode is responsive to 900-2500 nm. A combination of these two photodiodes can cover the spectral range of 200-2500 nm.

The LED array 120 and the first PD 140 are mounted to a first substrate 102. The second PD 150 and the focusing lens 152 are mounted to a second substrate 103. The first PD 140 and the second PD 150 may be simple photodiodes for minimizing the size of the sensing unit 100. Between the two substrates 102, 103 is the liquid-retaining space 104. Although the two substrates 102, 103 are drawn to be separate entities in FIG. 1, it is not intended to be a limitation for the present invention; it is possible that the two substrates 102, 103 are only different parts of a mechanical structure in the sensing unit 100.

The reflector 130 is located on the first substrate 102 such that an enclosed space 160 between the reflector 130 and the first substrate 102 is formed. The sensing unit 100 further comprises a sealer 165 formed by filling the enclosed space 160 with a substantially-transparent sealing material impermeable to the liquid. The sealer 165 is used for sealing the LED array 120 and the first PD 140 from the liquid. If the pre-determined liquid is water, one suitable water resistant polymer material such as resin, silicone, or polycarbonate, which is substantially transparent to light having a wavelength between 200 nm to 2500 nm, is used as the sealer 165. It is apparent that the emitted light propagated only inside the sealer 165 (i.e. the light rays 180a, 181a, 180d, 181b), including the refocused emitted light 181a-b, does not travel through the liquid. The sealer 165 is further prepared to have a convex surface 161 on the opening 136. In particular, the convex surface 161 is shaped to refract the emitted light incident on the opening 136 (i.e. the light rays 180b, 180c) to form the probe light beam 182a-b such that the probe light beam 182a-b is substantially collimated when the device is immersed in the liquid.

Figure 2:
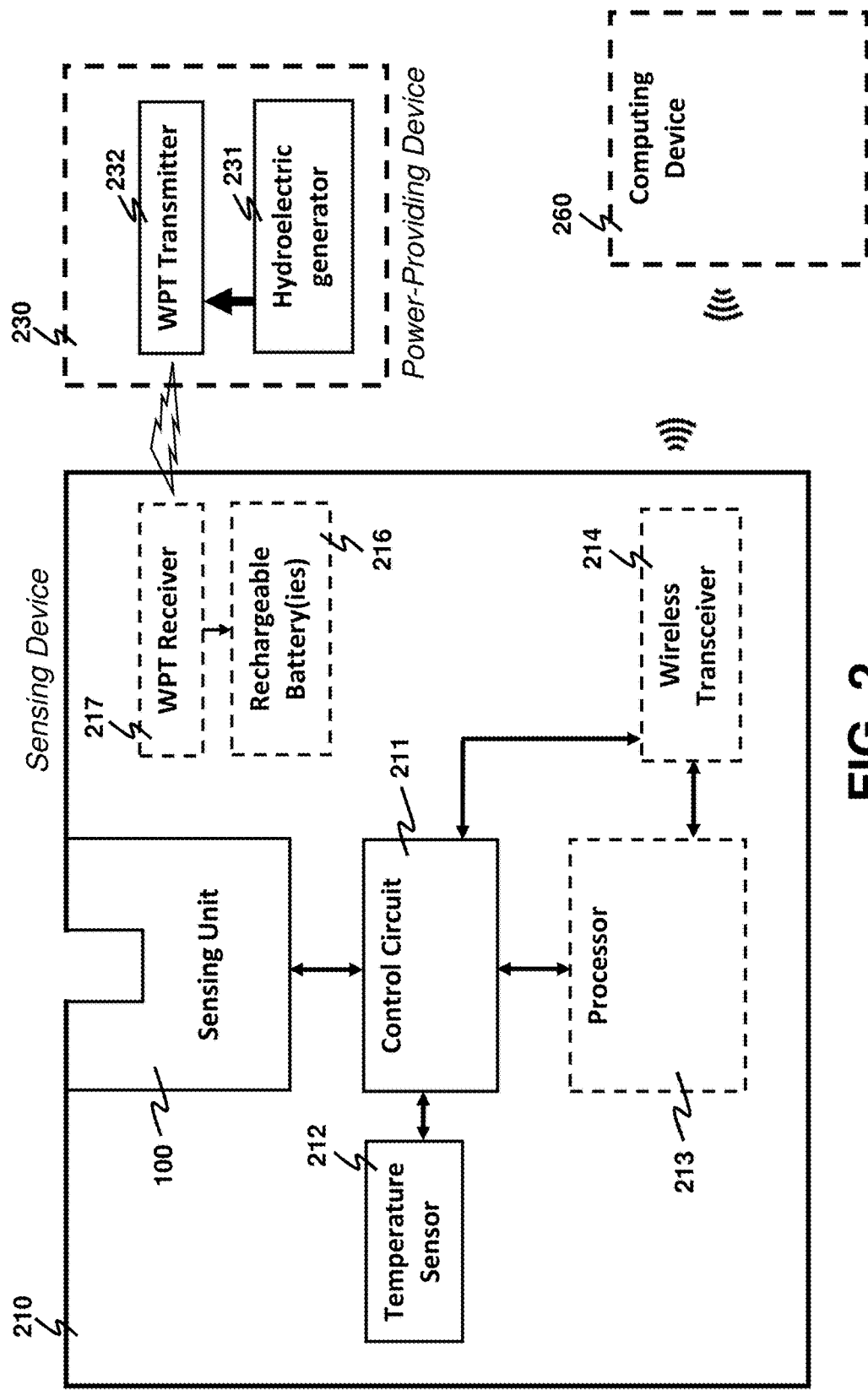
FIG. 2 depicts a schematic diagram of a device, including the sensing unit, for sensing a pre-determined liquid, where the device is optionally communicable with an external computing device for estimating an absorption spectrum of the liquid, and optionally receives energy from a power-providing device through wireless power transfer (WPT).

Integration of the sensing unit 100 with other functional units to form the sensing device is illustrated by referring to FIG. 2. FIG. 2 depicts an exemplary sensing device 210 that uses the sensing unit 100 to probe the liquid.

Since a simple photodetector is used in the second PD 150 to measure only the intensity of the measurement beam, the spectral information of the measurement beam is lost. To obtain the spectral information, the sensing device 210 comprises a control circuit 211 configured to control the LEDs 121-124 to sequentially generate the showers of light one-by-one such that plural pairs of intensity values are generated and received by the control circuit 211. Each pair of intensity values consists of the measured intensity and the reference intensity both obtained when an individual LED alone generates the emitted light 180a-d. The individual LED is selected from the LEDs 121-124.

As mentioned above, absorption peaks of the liquid directly identified from independent examination of each pair of intensity values are not unambiguous if there are partially-overlapped emission spectra among the LEDs 121-124. Consider a situation that at least two of the emission spectra of the LEDs 121-124 are partially overlapped. The pairs of intensity values are further computed to estimate the absorption spectrum of the liquid. This computation may be performed by a processor 213 in the sensing device 210 or by a computing device 260 external to the sensing device 210. The processor 213 means a computing processor. Examples of the computing device 260 include a smartphone and a tablet computer. Since this computation is generally intensive but the sensing device 210, usually battery-powered, has a limited power budget, using the computing device 260 to perform this computation is sometimes preferred. The computing device 260 communicates with the sensing device 210 through a cable or, more preferably and advantageously, via a wireless means. The sensing device 210 is wirelessly communicable with the computing device 260 by including a wireless transceiver 214. A wireless-communication protocol, such as a Bluetooth Low Energy (BLE) specification, may be used in achieving wireless communication between the sensing device 210 and the computing device 260.

Regardless of whether the processor 213 or the external computing device 260 is used to estimate the absorption spectrum, a necessary piece of information involved in the computation is a temperature of the LED array 120. The temperature affects the emission spectra of the LEDs 121-124 and also the peak wavelengths thereof. Hence, the sensing device 210 further incorporates a temperature sensor 212 controllable by the control circuit 211 for measuring the temperature of the LED array 120.

Figure 3A:
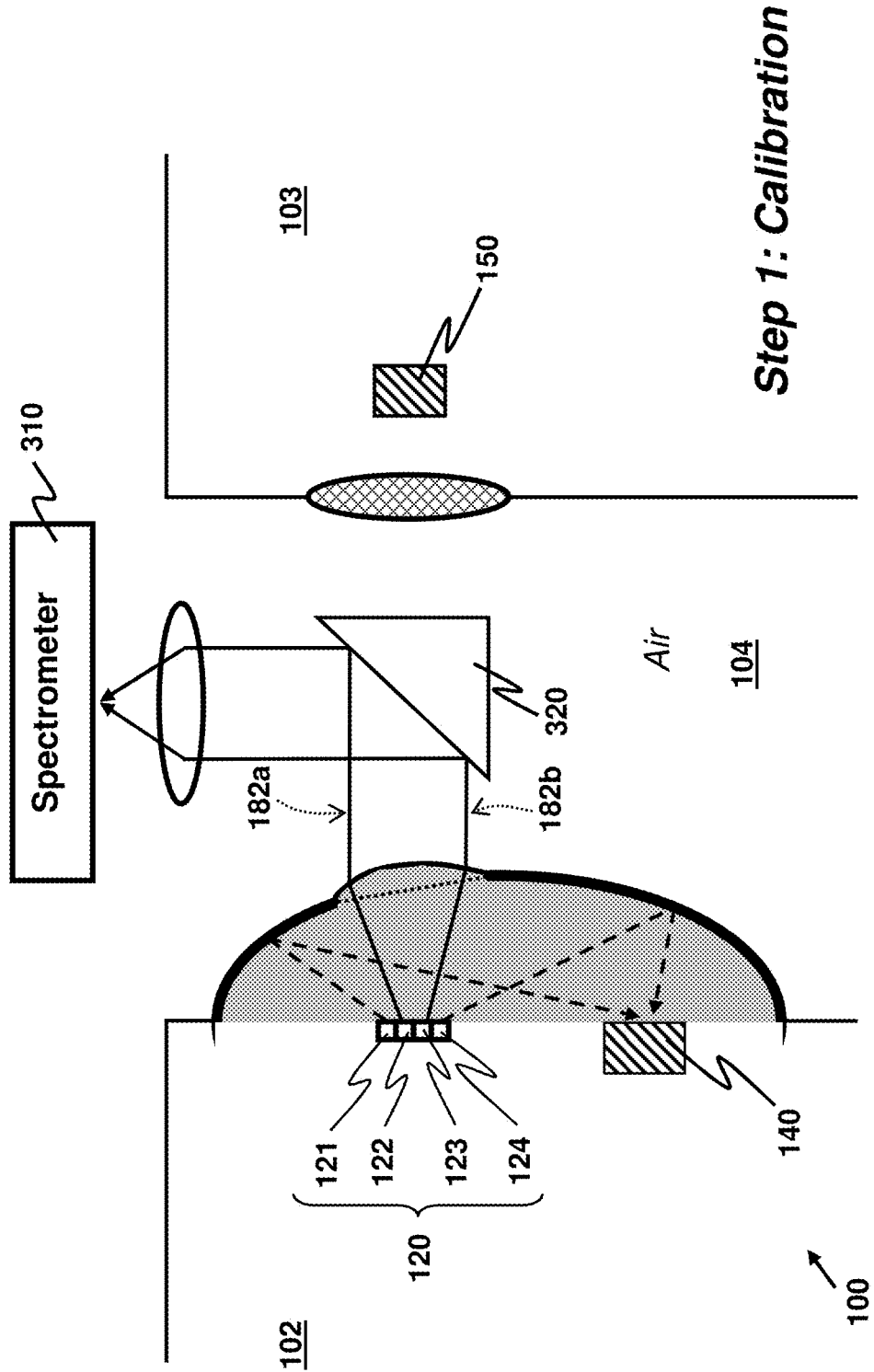
FIGS. 3A-3C exemplarily depict a process of obtaining an absorption spectrum of the liquid, where
Figure 3B:
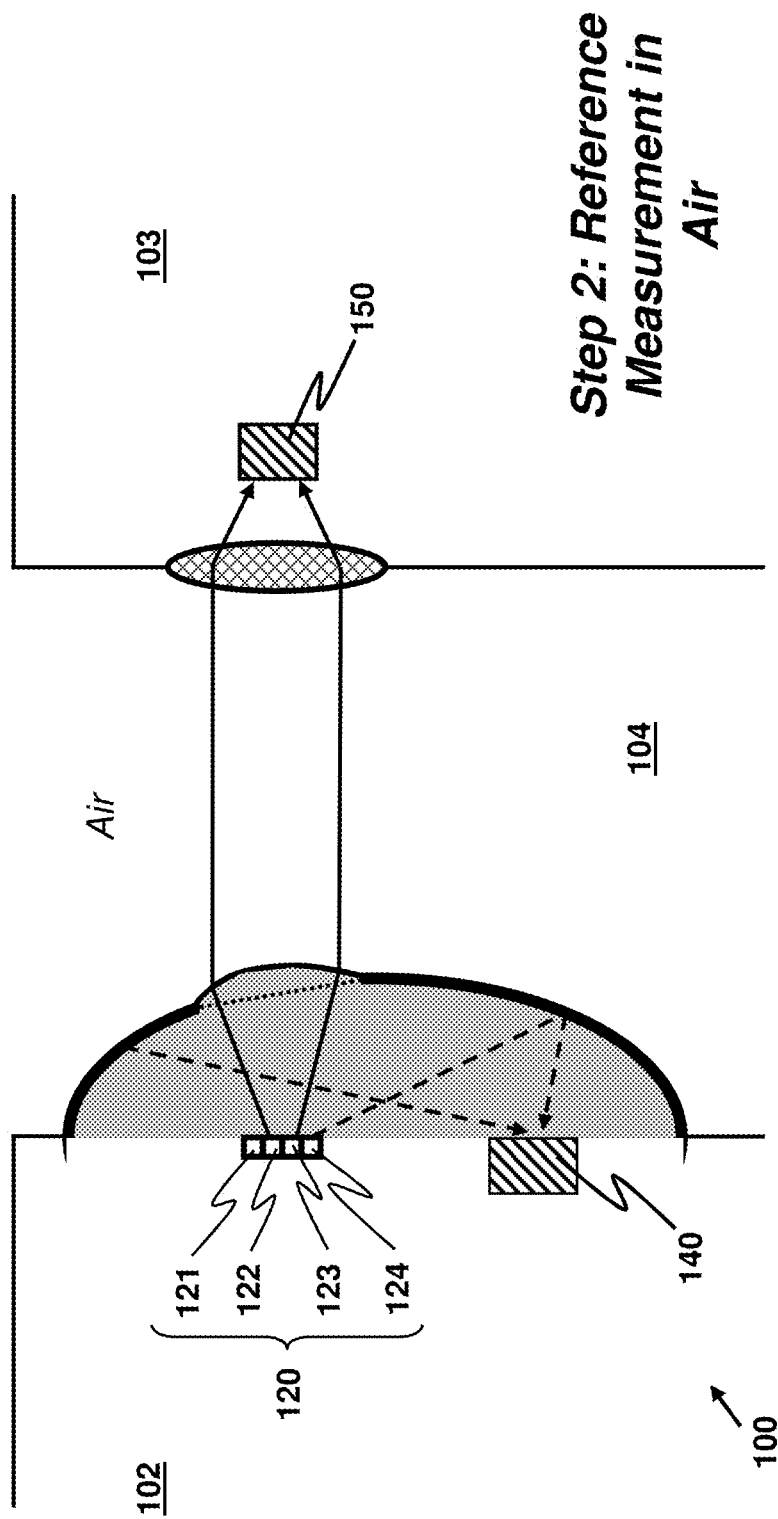
Figure 3C:
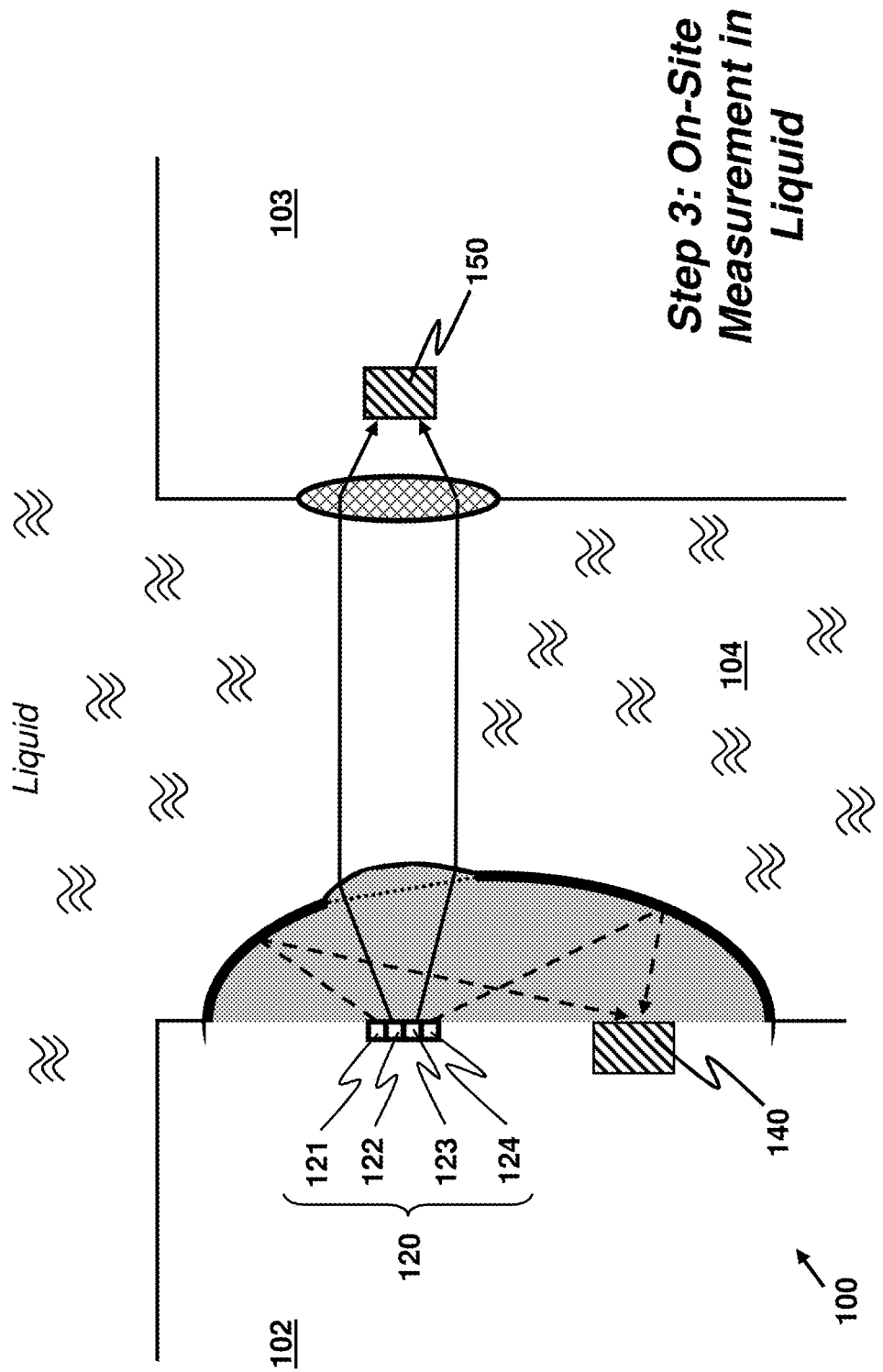

Exemplarily, a process of estimating the absorption spectrum from sensing the liquid involves three steps. FIG. 3A depicts a first step of calibrating emission spectra of LED under different values of temperature in order to fit each emission spectrum to a spectrum model. FIG. 3B depicts a second step of performing a reference measurement in air in order to compute reference spectra that are obtained at the first PD 140 and the second PD 150. FIG. 3C depicts a third step of performing on-site measurement for estimating the absorption spectrum of the liquid. In general, the first and second steps are preparatory steps performed in a controlled environment. The parameters obtained in the first and second steps are stored in a database of the sensing device 210 or of the computing device 260, depending on whether the processor 213 or the computing device 260 is used to estimate the absorption spectrum. The parameters are required in the estimation of the absorption spectrum from the data measured in the on-site measurement of the third step.

In the first step as shown in FIG. 3A, calibration of the emission spectra of each of the LEDs 121-124 in the LED array 120 under different temperatures is performed in a temperature-controllable chamber without being immersed in the liquid. The LEDs 121-124 sequentially generate the light showers one-by-one. When an individual LED generates a light shower, the probe light beam 182a-b heading to the second PD 150 is redirected, e.g., by a mirror 320, to a spectrometer 310 for spectral analysis, thereby obtaining an emission spectrum of the individual LED. The measured emission spectrum is fitted to a spectrum model and the necessary model parameters are estimated from the measured data. The spectrum model used here is an asymmetric Gaussian profile. Consider a LED i selected among the LEDs 121-124 in the LED array 120, where i is a LED index number. According to J. Y. Zhu, et al., "Synthesis of Spectral Distribution for LED-based Source with Tunable Spectra," *Chinese Journal of Luminescence*, vol. 31, pp. 882-887, 2010, the disclosure of which is incorporated by reference herein, the asymmetric Gaussian profile for the LED i under a temperature T is given by $$I_{i,T}(\lambda) = \alpha_{i,T} \exp\left(-\frac{4\ln(2)(\lambda - \lambda_{peak,i,T})^2}{[\beta_{i,T} + \gamma_{i,T}(\lambda_{peak,i,T} - \lambda)]^2}\right) \quad (1)$$

where: $I_{i,T}(\lambda)$ denotes a spectral intensity profile of the probe light beam 182a-b as a function of wavelength $\lambda$; $\lambda_{peak,i,T}$ is the peak wavelength; and $\alpha_{i,T}$, $\beta_{i,T}$ and $\gamma_{i,T}$ are model parameters for characterizing $I_{i,T}(\lambda)$. Note that: $\alpha_{i,T}$ is a scaling factor related to the total power carried by the probe light beam 182a-b produced by the LED i; both $\beta_{i,T}$ and $\gamma_{i,T}$ are shaping factors determining the shape of $I_{i,T}(\lambda)$; and $\lambda_{peak,i,T}$ relates to the peak position of $I_{i,T}(\lambda)$. As will soon be evident, $\alpha_{i,T}$ is not involved in the determination of the absorption spectrum. It follows that it is sufficient to store a set of $\{\beta_{i,T}, \gamma_{i,T}, \lambda_{peak,i,T}\}$ for different i's and T's in the database for future use. In one option, the range of T used in the calibration is from 10° C. to 40° C. with a 1° C. increment, covering most of practical situations for water sensing.

In the second step as shown in FIG. 3B, the reference measurement is also carried out in the temperature-controllable chamber without being immersed in the liquid. Different from the first step, the probe light beam 182a-b is not blocked or redirected, allowing the first PD 140 and the second PD 150 to give the reference intensity and the measured intensity, respectively. Similar to the first step, the LEDs 121-124 sequentially generate the light showers one-by-one. Denote $S'_{i,T,PD1}$ and $S'_{i,T,PD2}$ as the reference intensity and the measured intensity, respectively, obtained in the second step when the LED i is switched on to produce the light shower. By using the spectrum model of (1), one can model spectral intensity profiles of light received at the first PD 140 and at the second PD 150, respectively denoted as $I'_{i,T,PD1}(\lambda)$ and $I'_{i,T,PD2}(\lambda)$, by $$I'_{i,T,PD1}(\lambda) = \alpha'_{i,T,PD1} \exp\left(-\frac{4\ln(2)(\lambda - \lambda_{peak,i,T})^2}{[\beta_{i,T} + \gamma_{i,T}(\lambda_{peak,i,T} - \lambda)]^2}\right) \text{ and} \quad (2)$$

$$I'_{i,T,PD2}(\lambda) = \alpha'_{i,T,PD2} \exp\left(-\frac{4\ln(2)(\lambda - \lambda_{peak,i,T})^2}{[\beta_{i,T} + \gamma_{i,T}(\lambda_{peak,i,T} - \lambda)]^2}\right) \quad (3)$$

where $\alpha'_{i,T,PD1}$ and $\alpha'_{i,T,PD2}$ are corresponding scaling factors for $I'_{i,T,PD1}(\lambda)$ and $I'_{i,T,PD2}(\lambda)$, respectively. Note that in EQNS. (2) and (3), the values of $\beta_{i,T}$, $\gamma_{i,T}$ and $\lambda_{peak,i,T}$ are same as the ones used in characterizing (1) as these parameters are related to the shape and peak position of the spectral intensity profile. In addition, $$S'_{i,T,PD1} = \int_0^\infty I'_{i,T,PD1}(\lambda) d\lambda \quad (4)$$

and $$S'_{i,T,PD2} = \int_0^\infty I'_{i,T,PD2}(\lambda) d\lambda. \quad (4)$$

Since the values of $\beta_{i,T}$, $\gamma_{i,T}$ and $\lambda_{peak,i,T}$ are known from the database, the values of $\alpha'_{i,T,PD1}$ and $\alpha'_{i,T,PD2}$ can be numerically evaluated from $S'_{i,T,PD1}$ and $S'_{i,T,PD2}$, thereby allowing $I'_{i,T,PD1}(\lambda)$ and $I'_{i,T,PD2}(\lambda)$ to be fully characterized. It follows that $I'_{i,T,PD1}(\lambda)$ and $I'_{i,T,PD2}(\lambda)$ can be deconvoluted from the reference intensity and the measured intensity obtained from the first PD 140 and the second PD 150, respectively. The values of $\alpha'_{i,T,PD1}$ and $\alpha'_{i,T,PD2}$ for different i's and T's are also added to the database as model parameters to be used for the on-site measurement.

Figure 4:
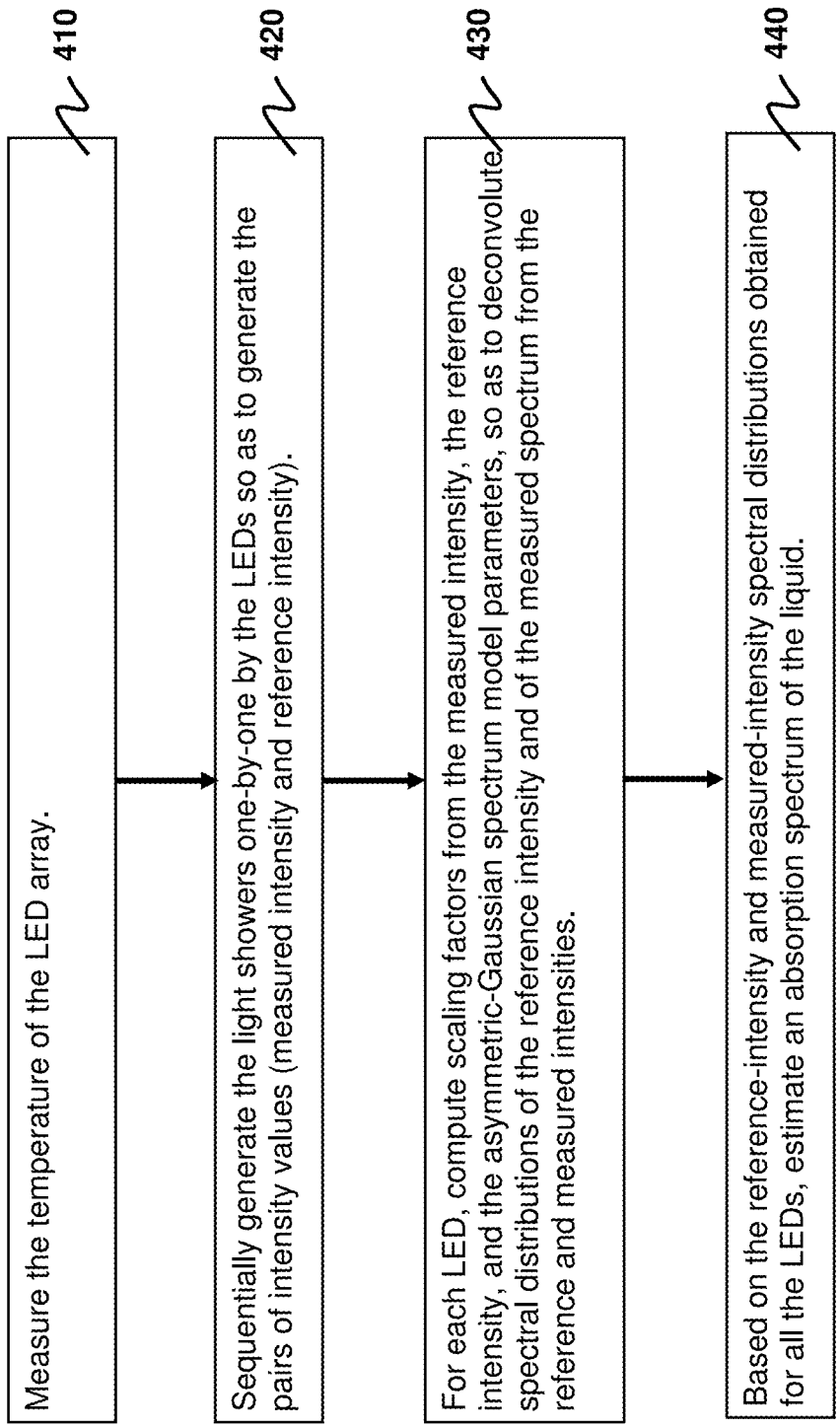
FIG. 4 depicts a flowchart for illustrating the steps of obtaining the absorption spectrum from sensing the liquid performed by the sensing unit in accordance with an exemplary embodiment of the present invention.

In the on-site measurement performed in the third step, the sensing device 210 is immersed in the liquid as shown in FIG. 3C. FIG. 4 is a flowchart exemplarily illustrating the steps performed in the on-site measurement.

First, it is necessary to measure the temperature T such that correct model parameters $\beta_{i,T}$, $\gamma_{i,T}$, etc. can be retrieved from the database for estimating the absorption spectrum. Therefore, in a step 410, either the processor 213 or the computing device 260, whichever appropriate, configures the control circuit 211 to command the temperature sensor 212 to measure the temperature of the LED array 120.

In a step 420, the control circuit 211 is configured to control, by either the processor 213 or the computing device 260, whichever appropriate, the LEDs 121-124 in the LED array 120 to sequentially generate the showers of light one-by-one. Meanwhile, the pairs of intensity values (each pair consisting of the reference intensity and the measured intensity) are generated and are received by the control circuit 211.

Denote $S''_{i,T,PD1}$ and $S''_{i,T,PD2}$ as the reference intensity and the measured intensity sensed by the first PD 140 and the second PD 150, respectively, when the LED i alone produces the shower of light and when the sensing device 210 performs the on-site measurement. Also denote $I''_{i,T,PD1}(\lambda)$ and $I''_{i,T,PD2}(\lambda)$ as the spectral distributions of the reference intensity and of the measured intensity, respectively, for the LED i. Using the spectrum model of (1) to model $I''_{i,T,PD1}(\lambda)$ and $I''_{i,T,PD2}(\lambda)$ gives $$I''_{i,T,PD1}(\lambda) = \alpha''_{i,T,PD1} \exp\left(-\frac{4\ln(2)(\lambda - \lambda_{peak,i,T})^2}{[\beta_{i,T} + \gamma_{i,T}(\lambda_{peak,i,T} - \lambda)]^2}\right) \text{ and} \quad (6)$$

$$I''_{i,T,PD2}(\lambda) = \alpha''_{i,T,PD2} \exp\left(-\frac{4\ln(2)(\lambda - \lambda_{peak,i,T})^2}{[\beta_{i,T} + \gamma_{i,T}(\lambda_{peak,i,T} - \lambda)]^2}\right) \quad (7)$$

where $\alpha''_{i,T,PD1}$ and $\alpha''_{i,T,PD2}$ are corresponding scaling factors characterizing $I''_{i,T,PD1}(\lambda)$ and $I''_{i,T,PD2}(\lambda)$ respectively. In a step 430, it is desired to determine $I''_{i,T,PD1}(\lambda)$ and $I''_{i,T,PD2}(\lambda)$ from $S''_{i,T,PD1}$ and $S''_{i,T,PD2}$. Since the model parameters $\beta_{i,T}$, $\gamma_{i,T}$ and $\lambda_{peak,i,T}$ under the temperature T are known from the database, it is only required to compute $\alpha''_{i,T,PD1}$ and $\alpha''_{i,T,PD2}$ for characterizing $I''_{i,T,PD1}(\lambda)$ and $I''_{i,T,PD2}(\lambda)$. As $$S''_{i,T,PD1} = \int_0^\infty I''_{i,T,PD1}(\lambda)d\lambda \tag{8}$$

and $$S''_{i,T,PD2} = \int_0^\infty I''_{i,T,PD2}(\lambda)d\lambda, \tag{9}$$

it follows that $\alpha''_{i,T,PD1}$ and $\alpha''_{i,T,PD2}$ can be obtained accordingly. Hence, $I''_{i,T,PD1}(\lambda)$ and $I''_{i,T,PD2}(\lambda)$ can be deconvoluted from $S''_{i,T,PD1}$ and $S''_{i,T,PD2}$, respectively. In the step 430, the obtaining of $I''_{i,T,PD1}(\lambda)$ and $I''_{i,T,PD2}(\lambda)$ is repeated for all the LEDs 121-124 in the LED array 120.

The processor 213 or the computing device 260, whichever appropriate, estimates the absorption spectrum of the liquid in a step 440. The absorption spectrum is given by a reciprocal of a transmittance spectrum of the liquid. The transmittance spectrum, denoted as $Y(\lambda)$, is given by $$Y(\lambda) = \left(\frac{\sum_i I''_{i,T,PD2}(\lambda)}{\sum_i I''_{i,T,PD1}(\lambda)}\right) \bigg/ \left(\frac{\sum_i I'_{i,T,PD2}(\lambda)}{\sum_i I'_{i,T,PD1}(\lambda)}\right). \tag{10}$$

It is apparent that $Y(\lambda)$ can be easily obtained by substituting EQNS. (2), (3), (6) and (7) into EQN. (10) with the model parameters $\beta_{i,T}$, $\gamma_{i,T}$, $\lambda_{peak,i,T}$, $\alpha'_{i,T,PD1}$ and $\alpha'_{i,T,PD2}$ stored in the database and with the computed values of $\alpha''_{i,T,PD1}$ and $\alpha''_{i,T,PD2}$.

Note that the steps 410, 420, 430 and 440 are used to estimate one absorption spectrum in one measurement. Those skilled in the art can easily adapt these steps in practical applications. In some practical applications, a user places the sensing device 210 at a location for doing continuous monitoring of water quality, and the sensing device 210 is required to be left unattended for a prolonged time before the user comes back to collect data from the sensing device 210. Those skilled in the art may program the control circuit 211 or the processor 213 to repeat the steps 410, 420, 430 and 440 at different time instants. The generated pairs of intensity values obtained at these different time instants are stored in the sensing device 210. When the user carrying the computing device 260 comes back, these generated pairs of intensity values are wirelessly transferred from the sensing device 210 to the computing device 260 through the wireless transceiver 214. The computing device 260 then repeats the steps 430 and 440 to estimate the absorption spectra measured at the different time instants.

One practical application of the sensing device 210 is to assess quality of water over a water distribution network in a building. In this application, it is often required to operate the sensing device 210 inside a water pipe that is difficult to access. Therefore, it is preferable if the sensing device 210 requires only minimum maintenance. Since the sensing device 210 is powered by one or more batteries, it is useful if the power consumption of the sensing device 210 can be kept low so that the one or more batteries need only be replaced infrequently. Alternatively, it is advantageous if some kind of energy harvesting can be achieved by the sensing device 210. Most desirably, the sensing device 210 can be self-powered. It is noticed that in the water pipe, water is frequently moving. The flowing water can be used as an energy source for the sensing device 210.

Refer to FIG. 2. The sensing device 210 is optionally configured to utilize motional energy of the liquid for fully or partially powering the sensing device 210. The sensing device 210 is powered by one or more on-board rechargeable batteries 216. In addition, the sensing device 210 receives energy from an external power-providing device 230 when both the sensing device 210 and the power-providing device 230 are immersed in the liquid. The power-providing device 230 is physically disconnected from the sensing device 210, and transfers energy thereto via inductive coupling according to a wireless-power-transfer (WPT) technique that is well-established in the art. The sensing device 210 includes a WPT receiver 217 for capturing wirelessly-transmitted electrical energy from the power-providing device 230 and using the captured electrical energy to recharge the one or more rechargeable batteries 216. The power-providing device 230 includes: a hydroelectric power generator 231 for harvesting motional energy of the liquid and converting the motional energy into electrical energy; and a WPT transmitter 232 for wirelessly delivering the electrical energy to the WPT receiver 217.

The sensing device 210 and the power-providing device 230 collectively form a subsystem for sensing the liquid. Optionally, an addition of the computing device 260 to the subsystem forms a system for measuring the absorption spectrum of the liquid.

The present invention may be embodied in other specific forms without departing from the spirit or essential characteristics thereof. The present embodiment is therefore to be considered in all respects as illustrative and not restrictive. The scope of the invention is indicated by the appended claims rather than by the foregoing description, and all changes that come within the meaning and range of equivalency of the claims are therefore intended to be embraced therein.

What is claimed is:

1. A device for sensing a pre-determined liquid, comprising a sensing unit, the sensing unit comprising:
    a light emitting diode (LED) array for emitting light, the LED array comprising plural LEDs;
    a reflector for reflecting light emitted from the LED array, the reflector including an opening for allowing a part of the emitted light to exit the reflector and form a probe light beam for sensing the liquid, the reflector being shaped to be substantially similar to one half of an ellipsoid except on the opening, the reflector having a first focus and a second focus, wherein the plural LEDs of the LED array are located at the first focus so that light emitted by the plural LEDs incident on the reflector is reflected to the second focus, causing the emitted light after reflection to be refocused at the second focus;
    a first photodetector (PD) located at the second focus and used for measuring an intensity of the refocused emitted light to thereby yield a reference intensity;
    a second PD for measuring an intensity of the probe light beam received after the probe light beam passes through the liquid to thereby yield a measured intensity;
    a substrate on which the LED array and the first PD are mounted, wherein the reflector is located on the substrate such that an enclosed space between the reflector and the substrate is formed; and a sealer formed by filling the enclosed space with a substantially-transparent sealing material impermeable to the liquid for sealing the LED array and the first PD from the liquid, wherein the sealer is further prepared to have a convex surface on the opening, the convex surface being shaped to refract the emitted light incident on the opening to form the probe light beam such that the probe light beam is substantially collimated when the device is immersed in the liquid.

2. The sensing device of claim 1, wherein the substantially-transparent sealing material is formed by liquid impermeable polymer.

3. The sensing device of claim 1, wherein each of the first and second PDs comprises one or more individual photodiodes collectively responsive to a spectral range of 200-2500 nm.

4. The sensing device of claim 1, wherein the pre-determined liquid is substantially composed of water.

5. The sensing device of claim 1, further comprising:
a control circuit for controlling at least the plural LEDs, the first PD and the second PD; wherein:
each of the plural LEDs generates a shower of light having an emission spectrum having a single dominant spectral peak at a peak wavelength, the peak wavelengths of the plural LEDs being distinct; and
the control circuit controls the plural LEDs to sequentially generate the showers of light one-by-one such that plural pairs of intensity values are generated and received by the control circuit, each pair of intensity values consisting of the measured intensity and the reference intensity both obtained when an individual LED alone generates the emitted light.

6. The sensing device of claim 5, further comprising:
a temperature sensor for measuring a temperature of the LED array, the temperature sensor being controllable by the control circuit.

7. The sensing device of claim 6, further comprising:
a processor for estimating an absorption spectrum of the liquid according to the pairs of intensity values.

8. The sensing device of claim 7, wherein the processor executes a process of estimating the absorption spectrum, the process comprising the steps of:
(a) causing the control circuit to:
control the LEDs to sequentially generate the showers of light one-by-one so as to generate the pairs of intensity values; and
measure the temperature of the LED array;
(b) receiving the pairs of intensity values and the LED array temperature;
(c) for the individual LED:
computing a first scaling factor of an asymmetric Gaussian spectrum model for characterizing a first spectral distribution of the reference intensity according to the reference intensity and a set of pre-determined model parameters of the asymmetric Gaussian spectrum model, wherein the set of pre-determined model parameters, specific to the individual LED, is selected from a larger set of pre-determined model parameters based on the measured temperature; and
computing a second scaling factor of the asymmetric Gaussian spectrum model for characterizing a second spectral distribution of the measured intensity according to the measured intensity and the set of pre-determined model parameters;

(d) repeating step (c) for all the LEDs in the LED array, such that a plurality of first spectral distributions and a plurality of second spectral distributions are obtained; and
(e) obtaining the absorption spectrum according to the plurality of first spectral distributions and the plurality of second spectral distributions.

9. A system for measuring an absorption spectrum of a pre-determined liquid, comprising:
the sensing device of claim 6; and
a computing device communicable with the sensing device, wherein the computing device estimates the absorption spectrum of the liquid according to the pairs of intensity values received from the sensing device.

10. A method for measuring an absorption spectrum of a pre-determined liquid, comprising the steps of:
(a) providing the sensing device of claim 6;
(b) causing the control circuit to:
control the LEDs to sequentially generate the showers of light one-by-one so as to generate the pairs of intensity values; and
measure the temperature of the LED array;
(c) for the individual LED:
computing a first scaling factor of an asymmetric Gaussian spectrum model for characterizing a first spectral distribution of the reference intensity according to the reference intensity and a set of pre-determined model parameters of the asymmetric Gaussian spectrum model, wherein the set of pre-determined model parameters, specific to the individual LED, is selected from a larger set of pre-determined model parameters based on the measured temperature; and
computing a second scaling factor of the asymmetric Gaussian spectrum model for characterizing a second spectral distribution of the measured intensity according to the measured intensity and the set of pre-determined model parameters;
(d) repeating step (c) for all the LEDs in the LED array, such that a plurality of first spectral distributions and a plurality of second spectral distributions are obtained; and
(e) obtaining the absorption spectrum according to the plurality of first spectral distributions and the plurality of second spectral distributions.

11. The method of claim 10, wherein in step (e), the absorption spectrum is given by a reciprocal of a transmittance spectrum of the liquid, the transmittance spectrum, $Y(\lambda)$, being given by $$Y(\lambda) = \left(\frac{\sum_i I''_{i,T,PD2}(\lambda)}{\sum_i I''_{i,T,PD1}(\lambda)}\right) \Big/ \left(\frac{\sum_i I'_{i,T,PD2}(\lambda)}{\sum_i I'_{i,T,PD1}(\lambda)}\right)$$

where:
i denotes a LED index number of the individual LED;

$$I''_{i,T,PD1}(\lambda) = \alpha''_{i,T,PD1} \exp\left(-\frac{4\ln(2)(\lambda - \lambda_{peak,i,T})^2}{[\beta_{i,T} + \gamma_{i,T}(\lambda_{peak,i,T} - \lambda)]^2}\right);$$

$$I''_{i,T,PD2}(\lambda) = \alpha''_{i,T,PD2} \exp\left(-\frac{4\ln(2)(\lambda - \lambda_{peak,i,T})^2}{[\beta_{i,T} + \gamma_{i,T}(\lambda_{peak,i,T} - \lambda)]^2}\right);$$

-continued $$I'_{i,T,PD1}(\lambda) = \alpha'_{i,T,PD1}\exp\left(-\frac{4\ln(2)(\lambda-\lambda_{peak,i,T})^2}{[\beta_{i,T}+\gamma_{i,T}(\lambda_{peak,i,T}-\lambda)]^2}\right);$$

$$I'_{i,T,PD2}(\lambda) = \alpha'_{i,T,PD2}\exp\left(-\frac{4\ln(2)(\lambda-\lambda_{peak,i,T})^2}{[\beta_{i,T}+\gamma_{i,T}(\lambda_{peak,i,T}-\lambda)]^2}\right);$$

$\beta_{i,T}$, $\gamma_{i,T}$, $\lambda_{peak,i,T}$, $\alpha'_{i,T,PD1}$ and $\alpha'_{i,T,PD2}$ are provided from the set of pre-determined model parameters; and $\alpha''_{i,T,PD1}$ and $\alpha''_{i,T,PD2}$ are the first scaling factor and the second scaling factor, respectively, obtained in step (c).

12. The sensing device of claim 6, further comprising:
a wireless transceiver for enabling the sensing device to wirelessly communicate with an external computing device.

13. The sensing device of claim 6, wherein each of the peak wavelengths of LEDs of the LED array is between 200 nm and 2500 nm.

14. The sensing device of claim 6, further comprising:
one or more rechargeable batteries for powering the sensing device; and
a wireless-power-transfer (WPT) receiver for capturing wirelessly-transmitted electrical energy and using the captured electrical energy to recharge the one or more rechargeable batteries.

15. A subsystem for sensing the liquid, comprising:
the sensing device of claim 14; and
a power-providing device for providing electrical energy to the sensing device without physically contacting the sensing device when the sensing device is immersed in the liquid, wherein the power-providing device comprises:
a hydroelectric power generator for harvesting motional energy of the liquid and converting the motional energy into electrical energy; and
a WPT transmitter for wirelessly delivering the electrical energy to the WPT receiver.

16. The subsystem of claim 15, wherein the sensing device further comprises:
a processor for estimating an absorption spectrum of the liquid according to the pairs of intensity values.

17. A system for measuring an absorption spectrum of a pre-determined liquid, comprising:
the subsystem of claim 15; and
a computing device communicable with the sensing device, wherein the computing device estimates the absorption spectrum of the liquid according to the pairs of intensity values received from the sensing device.

18. A method for measuring an absorption spectrum of a pre-determined liquid, comprising:
(a) providing the subsystem of claim 15;
(b) causing the control circuit to:
control the LEDs to sequentially generate the showers of light one-by-one so as to generate the pairs of intensity values; and
measure the temperature of the LED array;
(c) for the individual LED:
computing a first scaling factor of an asymmetric Gaussian spectrum model for characterizing a first spectral distribution of the reference intensity according to the reference intensity and a set of pre-determined model parameters of the asymmetric Gaussian spectrum model, wherein the set of pre-determined model parameters, specific to the individual LED, is selected from a larger set of pre-determined model parameters based on the measured temperature; and
computing a second scaling factor of the asymmetric Gaussian spectrum model for characterizing a second spectral distribution of the measured intensity according to the measured intensity and the set of pre-determined model parameters;
(d) repeating step (c) for all the LEDs in the LED array, such that a plurality of first spectral distributions and a plurality of second spectral distributions are obtained; and
(e) obtaining the absorption spectrum according to the plurality of first spectral distributions and the plurality of second spectral distributions.

19. The sensing device of claim 1, further comprising:
one or more rechargeable batteries for powering the sensing device; and
a wireless-power-transfer (WPT) receiver for capturing wirelessly-transmitted electrical energy and using the captured electrical energy to recharge the one or more rechargeable batteries.

20. A subsystem for sensing the liquid, comprising:
the sensing device of claim 19; and
a power-providing device for providing electrical energy to the sensing device without physically contacting the sensing device when the sensing device is immersed in the liquid, wherein the power-providing device comprises:
a hydroelectric power generator for harvesting motional energy of the liquid and converting the motional energy into electrical energy; and
a WPT transmitter for wirelessly delivering the electrical energy to the WPT receiver.

* * * * *

UNITED STATES PATENT AND TRADEMARK OFFICE
CERTIFICATE OF CORRECTION

PATENT NO. : 10,161,861 B2
APPLICATION NO. : 15/377643
DATED : December 25, 2018
INVENTOR(S) : Chun Zhang et al.

Page 1 of 1

It is certified that error appears in the above-identified patent and that said Letters Patent is hereby corrected as shown below:

In the Specification

At Column 9, Line number 36, delete "$\alpha'_{i,T,PD2}$" and replace with --$\alpha''_{i,T,PD2}$--.

In the Claims

At Column 12, Claim number 11, Line number 50, delete "Y(A)" and replace with --Y($\lambda$)--.

Signed and Sealed this
Twenty-sixth Day of February, 2019

Andrei Iancu
*Director of the United States Patent and Trademark Office*